United States Patent [19]
Drabek

[11] 3,982,015
[45] Sept. 21, 1976

[54] N-PROPARGYL-ANILINOMETHYLENEMALODINITRILE DERIVATIVES
[75] Inventor: Jozef Drabek, Allschwil, Switzerland
[73] Assignee: Ciba-Geigy Corporation, Ardsley, N.Y.
[22] Filed: Aug. 5, 1975
[21] Appl. No.: 602,055

[30] Foreign Application Priority Data
Aug. 14, 1974  Switzerland............... 11137/74
Aug. 14, 1974  Switzerland............... 11138/74
June 25, 1975  Switzerland............... 8253/75

[52] U.S. Cl. .................. 424/304; 260/465 E
[51] Int. Cl.² ............... A01N 9/20; C07C 121/78
[58] Field of Search ............. 260/465 E; 424/304

[56] References Cited
UNITED STATES PATENTS
3,551,573  12/1970  Baker et al. ............... 424/304

Primary Examiner—Lewis Gotts
Assistant Examiner—Dolph H. Torrence
Attorney, Agent, or Firm—Harry Falber; Frederick H. Rabin

[57] ABSTRACT

Compounds of the formula I

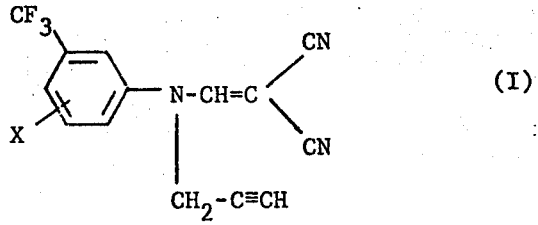

wherein X is trifluoromethyl, chlorine, bromine or iodine as novel agents having insecticidal properties.

15 Claims, No Drawings

N-PROPARGYL-ANILINOME-THYLENEMALODINITRILE DERIVATIVES

The present invention provides novel N-propargylanilinomethylenemalodinitrile derivatives which act against pests, a process for the manufacture thereof, pesticidal compositions which contain said derivatives as active principle, and a method of combating pests which comprises the use of the novel derivatives.

The invention provides in particular the N-propargylanilinomethylenemalodinitrile derivatives of the formula I

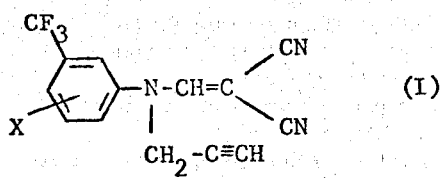

wherein X represents a trifluoromethyl group or a chlorine, fluorine, bromine or iodine atom.

Preferred compounds are those of the formula I wherein X represents a trifluoromethyl group or a chlorine or bromine, especially a chlorine, atom, e.g. N-propargyl-(3,5-bis-trifluoromethylanilino)-, N-propargyl-(4-chloro-3-trifluoromethylanilino)-, N-propargyl-(5-chloro-3-trifluoromethylanilino)-, N-propargyl-(6-chloro-3-trifluoromethylanilino)- and N-propargyl-(4-bromo-3-trifluoromethylanilino)-methylenemalodinitrile.

The compounds of the formula I are manufactured by the following processes which are known per se which comprise a. reacting an anilinomethylenemalodinitrile of the formula II

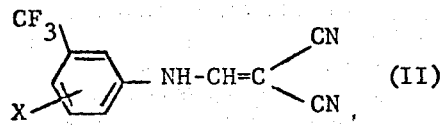

wherein X has the meaning given under formula I, with a propargyl halide of the formula III

wherein Hal represents a halogen atom, especially a chlorine, bromine or iodine atom, in the presence of a base, or b. reacting the potassium, sodium or ammonium salt of an anilinomethylenemalodinitrile of the formula II above with a propargyl halide of the formula III above.

Examples of suitable bases which can be used for this reaction are tertiary amines, e.g. triethylamine, dimethyl aniline and pyridine; alcoholates of alkaline metals, e.g. sodium methylate and potassium tert. butylate; and inorganic bases, such as the hydrides, hydroxides and carbonates of alkali metals and alkaline earth metals.

The reaction is preferably carried out at normal pressure and at a temperature between 0° and 120°C in a solvent or diluent which is inert to the reactants.

Examples of suitable solvents or diluents are: aromatic and halogenated hydrocarbons, e.g. benzene, toluene, chlorobenzene, polychlorobenzenes, bromobenzene and chlorinated alkanes of 1 to 3 carbon atoms; ethers, e.g. dioxan and tetrahydrofuran; esters, e.g. ethyl acetate; ketones, e.g. acetone, methyl ethyl ketone and diethyl ketone; formamide; nitriles, e.g. acetonitrile; alcohols, e.g. ethyl alcohol; as well as dimethyl sulphoxide and water.

The starting materials of the formula II and II are known and can be manufactured by known methods. A method of manufacturing the starting materials of the formula II is described for example in U.S. Pat. No. 3,551,573.

The compounds of the formula I are suitable for combating insects, in particular insects that damage ornamental and useful plants, e.g. fruit and vegetables by eating, and above all for combating insect parasites in rice and cotton plantations, e.g. *Chilo suppressalis, Spodoptera littoralis* and *Heliothis virescens*. The compounds of the formula I can therefore be used for example against insect parasites of the families:

Acrididae, Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelisae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae, and Pulicidae.

The insecticidal or acaricidal action can be substantially broadened and adapted to given circumstances by addition of other insecticides and/or acaricides. Examples of suitable additives are: organic phosphorus compounds, nitrophenols and derivatives, formamidines, ureas, pyethroids, carbamates, and/or chlorinated hydrocarbons.

The compounds of the formula I may be used as pure active substance or together with suitable carriers and/or additives. Suitable carriers and additives can be solid or liquid and correspond to the substances conventionally used in formulation technology, for example natural or regenerated substances, solvents, dispersants, wetting agents, stickers, thickeners, binders and/or fertilisers.

For application, the compounds of the formula I may be processed to dusts, emulsion concentrates, granules, dispersions, sprays, to solutions, or suspensions, in the conventional formulation which is commonly employed in application technology.

The compositions according to the invention are manufactured in known manner by intimately mixing and/or grinding active substances of the formula I with the suitable carriers, optionally with the addition of dispersants or solvents which are inert to the active substances.

The active substances may take, and be used in, the following forms:

Solid forms:
Dusts, tracking agents, granules, coated granules, impregnated granules and homogeneous granules.
Liquid forms:
a. active substances which are dispersible in water: wettable powders, pastes, emulsions;
b. solutions.

The content of active substance in the above described compositions is between 0.1 to 95%.

The active substances of the formula I can, for example, be formulated as follows:

Dusts

The following substances are used to manufacture a. a 5% and
b. a 2% dust:

a.
5 parts of active substance,
95 parts of talcum;

b.
2 parts of active substance,
1 part of highly disperse silicic acid,
97 parts of talcum.

The active substances are mixed with the carriers and ground.

Granules

The following substances are used to produce 5% granules:
5 parts of active substance,
0.25 parts of epichlorohydrin,
0.25 parts of cetyl polyglycol ether,
3.50 parts of polyethylene glycol,
91 parts of kaolin (particle size 0.3 – 0.8 mm).

The active substance is mixed with epichlorohydrin and dissolved with 6 parts of acetone; the polyethylene glycol and cetyl polyglycol ether are then added. The resultant solution is sprayed on kaolin, and the acetone is subsequently evaporated in vacuo.

Wettable powder:

The following constituents are used for the preparation of (a) a 40%, (b) and (c) a 25%, and (d) a 10% wettable powder:

a.
40 parts of active substance,
5 parts of sodium lignin sulphonate,
1 part of sodium dibutyl-naphthalene sulphonate,
54 parts of silicic acid.

b.
25 parts of active substance,
4.5 parts of calcium lignin sulphonate,
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin.

c.
25 parts of active substance,
2.5 parts of isooctylphenoxy-polyoxyethyleneethanol,
1.7 parts of Champagne chalk/hydroxyethyl cellulose mixture (1:1),
8.3 parts of sodium aluminium silicate,
16.5 parts of kieselgur,
46 parts of kaolin.

d.
10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates:

The following substances are used to produce (a) a 10% and (b) a 25% emulsifiable concentrate:

a.
10 parts of active substance,
3.4 parts of epoxidised vegetable oil,
13.4 parts of a combination emulsifier consisting of fatty alcohol polyglycol ether and alkyl aryl sulphonate calcium salt,
40 parts of dimethylformamide,
43.2 parts of xylene, b.
25 parts of active substance,
2.5 parts of epoxidised vegetable oil,
10 parts of an alkylarylsulphonate/fatty alcoholglycol ether mixture,
5 parts of dimethylformamide,
57.5 parts of xylene.

By diluting such concentrates with water it is possible to manufacture emulsions of every desired concentration.

Spray:

The following constituents are used to prepare (a) a 5% and (b) a 95% spray:

a.
5 parts of active substance,
1 part of epichlorohydrin,
94 part of benzene (boiling limits 160°–190°C).

b.
95 parts of active substance,
5 parts of epichlorohydrin.

The following Examples illustrate the invention in more detail.

EXAMPLE 1

Manufacture of N-propargyl-(3,5-bis-trifluoromethylanilino)-methylenemalodinitrile (compound 1):

30.4 g of 3,5-trifluoromethylanilinomethylenemalonic acid dinitrile are dissolved in a solution of 5.61 g of potassium hydroxide in 100 ml of methanol and the resultant solution is evaporated to dryness. The residue is dissolved in 150 ml of acetonitrile and the solution is treated with 11.9 g of propargyl bromide. The mixture is stirred for 3 hours at 50°C and then filtered. The solvent is distilled of and the residue is dissolved in chloroform. The chloroform solution is filtered and the chloroform is distilled off to yield 20.3 g of the compound of the formula

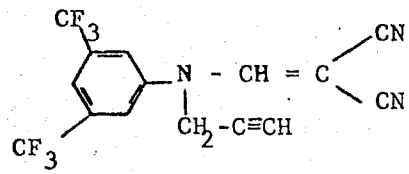

with a melting point of 104°–107°C (recrystallised from methanol/water).

The following compounds were also manufactured in analogous manner:

2. N-propargyl-(4-chloro-3-trifluoromethylanilino)-methylenemalodinitrile (m.p. 94°–96°C).

3. N-propargyl-(4-bromo-3-trifluoromethylanilino)-methylenemalodinitrile.
4. N-propargyl-(6-chloro-3-trifluoromethylanilino)-methylenemalodinitrile (m.p. 82°C).

EXAMPLE 2

Insecticidal stomach poison action

Cotton and potato plants were sprayed with a 0.05% aqueous emulsion of active substance (obtained from a 10% emulsifiable concentrate). After the spray coating had dried, the cotton plants were populated with *Spodoptera littoralis* or *Heliothis virescens* larvae $L_3$ and the potato plants with Colorado potato beetle larvae (Leptinotarsa decemlineata). The experiment was carried out at 24°C and 60% relative humidity.

In this experiment, the compounds according to Example 1 demonstrated a good insecticidal stomach poison action against *Spodoptera littoralis*, *Heliothis virescens* and *Leptinotarsa decemlineata* larvae.

EXAMPLE 3

Action against *chilo suppressalis*

Six rice plants at a time of the Caloro variety were transplanted into plastic pots with a diameter of 17 cm at the top and reared to a height of about 60 cm. Infestation with *Chilo suppressalis* larvae ($L_1$; 3–4 mm in length) took place 2 days after the active substance had been applied in granule form to the paddy water (rate of application: 8 kg of active substance/ha). Evaluation of the insecticidal action was carried out 10 day after the application of the granules. Compound 1 of Example 1 demonstrated in this experiment a good action against *Chilo suppressalis* $L_1$ larvae.

I claim:
1. Compounds of the formula I

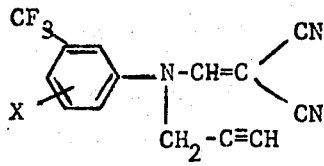

(I)

wherein X represents trifluoromethyl, chlorine, fluorine, bromine or iodine.

2. Compounds according to claim 1, wherein X represents trifluoromethyl or chlorine.
3. N-propargyl-(3,5-bis-trifluoromethylanilino)-methylenemalodinitrile according to claim 1.
4. N-propargyl-(4-chloro-3-trifluoromethylanilino)-methylenemalodinitrile according to claim 1.
5. N-propargyl-(4-bromo-3-trifluoromethylanilino)-methylenemalodinitrile according to claim 1.
6. N-propargyl-(6-chloro-3-trifluoromethylanilino)-methylenemalodinitrile according to claim 1.
7. An insecticidal composition which contains as active component an insecticidally effective amount of a compound according to claim 1, together with a suitable carrier therefor.
8. A method for combatting insects which comprises applying to the locus thereof an insecticidally effective amount of a compound according to claim 1.
9. The method of claim 8, wherein in said compound X represents trifluoromethyl or chlorine.
10. The method of claim 8, wherein said compound is N-propargyl-(3,5-bis-trifluoromethylanilino)-methylenemalodinitrile.
11. The method of claim 8, wherein said compound is N-propargyl-(4-chloro-3-trifluoromethylanilino)-methylenemalodinitrile.
12. The method of claim 8, wherein said compound is N-propargyl-(4-bromo-3-trifluoromethylanilino)-methylenemalodinitrile.
13. The method of claim 8, wherein said compound is N-propargyl-(6-chloro-3-trifluoromethylanilino)-methylenemalodinitrile
14. The method according to claim 8, wherein the locus comprises agricultural or horticultural crops of plants.
15. The method of claim 14, wherein the locus comprises rice or cotton crops.

* * * * *